(12) United States Patent
Donegan (10) Patent No.: US 11,219,744 B2
(45) Date of Patent: Jan. 11, 2022

(54) PUSH WIRE FOR ENDOLUMINAL MEDICAL DEVICE

(71) Applicant: Medtronic Vascular, Inc., Santa Rosa, CA (US)

(72) Inventor: Michael Donegan, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 694 days.

(21) Appl. No.: 15/493,327

(22) Filed: Apr. 21, 2017

(65) Prior Publication Data

US 2018/0304042 A1 Oct. 25, 2018

(51) Int. Cl.
| | |
|---|---|
| A61M 25/01 | (2006.01) |
| A61M 25/00 | (2006.01) |
| A61M 25/10 | (2013.01) |
| A61M 25/09 | (2006.01) |
| A61L 29/10 | (2006.01) |
| A61L 29/14 | (2006.01) |
| A61L 29/02 | (2006.01) |

(52) U.S. Cl.
CPC ......... *A61M 25/0102* (2013.01); *A61L 29/02* (2013.01); *A61L 29/103* (2013.01); *A61L 29/106* (2013.01); *A61L 29/14* (2013.01); *A61M 25/0045* (2013.01); *A61M 25/09* (2013.01); *A61M 25/10* (2013.01); *A61M 2025/0046* (2013.01); *A61M 2025/09075* (2013.01); *A61M 2025/09133* (2013.01); *A61M 2025/1079* (2013.01); *A61M 2205/025* (2013.01)

(58) Field of Classification Search
CPC .... A61M 2205/025; A61M 2025/1079; A61M 2025/09133; A61M 2025/09075; A61M 2025/0046; A61M 25/10; A61M 25/09; A61M 25/0102; A61M 25/0045
See application file for complete search history.

(56) References Cited

U.S. PATENT DOCUMENTS

| | | | | |
|---|---|---|---|---|
| 4,941,473 A | * | 7/1990 | Tenerz | A61B 5/0215 600/434 |
| 5,069,226 A | * | 12/1991 | Yamauchi | A61L 31/022 600/585 |
| 5,238,004 A | * | 8/1993 | Sahatjian | A61M 25/09 600/434 |
| 5,558,093 A | * | 9/1996 | Pomeranz | A61B 8/12 600/439 |

(Continued)

FOREIGN PATENT DOCUMENTS

| | | | | |
|---|---|---|---|---|
| JP | 07124262 A | * | 10/1993 | ............ A61M 25/01 |
| JP | 2000000297 A | | 1/2000 | |

(Continued)

OTHER PUBLICATIONS

IP.com Translation of JP 2001-333986 A, Published on Dec. 4, 2011, Mashashi, Momota and Tomihisa, Kato.*

(Continued)

*Primary Examiner* — Sean P Dougherty
(74) *Attorney, Agent, or Firm* — Mueting Raasch Group (57) ABSTRACT

An elongate body extending from a proximal end to a distal end includes a core comprising an amorphous metal alloy and includes a sheath that comprises a crystalline metallic material. The sheath surrounds the core.

21 Claims, 4 Drawing Sheets

(56) References Cited

U.S. PATENT DOCUMENTS

| | | | | |
|---|---|---|---|---|
| 5,588,443 | A | * | 12/1996 | Davidson ............. A61F 2/0077 600/585 |
| 5,673,707 | A | * | 10/1997 | Chandrasekaran ... A61M 25/09 600/434 |
| 6,165,140 | A | * | 12/2000 | Ferrera ................. A61M 25/09 600/585 |
| 6,340,441 | B1 | * | 1/2002 | Meyer ..................... B29C 48/13 264/173.12 |
| 6,402,859 | B1 | * | 6/2002 | Ishii ....................... A61L 29/02 148/421 |
| 6,436,056 | B1 | * | 8/2002 | Wang ................. A61M 25/104 600/585 |
| 6,767,418 | B1 | * | 7/2004 | Zhang .................... A61L 27/06 148/421 |
| 7,011,636 | B2 | * | 3/2006 | Tenerz ................. A61B 5/0215 600/585 |
| 8,057,530 | B2 | | 11/2011 | Kusleika et al. |
| 8,387,347 | B2 | * | 3/2013 | Imai ..................... A61L 29/041 53/425 |
| 8,579,825 | B2 | * | 11/2013 | Tenerz ................. A61M 25/09 600/488 |
| 2002/0087100 | A1 | * | 7/2002 | Onuki ................. A61B 1/00098 600/585 |
| 2002/0162605 | A1 | * | 11/2002 | Horton, Jr. ........... A61B 17/866 148/304 |
| 2002/0188188 | A1 | * | 12/2002 | Hiejima ................ A61M 25/09 600/407 |
| 2003/0083622 | A1 | * | 5/2003 | Osawa .................. A61M 25/09 604/164.13 |
| 2003/0093110 | A1 | * | 5/2003 | Vale ........................ A61F 2/013 606/200 |
| 2003/0120181 | A1 | * | 6/2003 | Toma ...................... A61L 31/14 600/585 |
| 2005/0101836 | A1 | * | 5/2005 | Onuki ................ A61B 1/00098 600/104 |
| 2008/0125848 | A1 | * | 5/2008 | Kusleika ................. A61L 29/02 623/1.11 |
| 2008/0161727 | A1 | * | 7/2008 | Aimi ..................... A61M 25/09 600/585 |
| 2010/0023035 | A1 | * | 1/2010 | Kontos .......... A61B 17/320725 606/159 |
| 2010/0211048 | A1 | * | 8/2010 | Arai ...................... A61M 25/09 604/528 |
| 2011/0009806 | A1 | * | 1/2011 | Melsheimer .......... A61M 25/09 604/21 |
| 2012/0022634 | A1 | | 1/2012 | Kusleika et al. |
| 2014/0138570 | A1 | * | 5/2014 | Otsuka ..................... H01F 1/24 252/62.55 |
| 2015/0231368 | A1 | * | 8/2015 | Hsueh ............... A61M 25/0084 604/510 |

FOREIGN PATENT DOCUMENTS

| | | |
|---|---|---|
| JP | 2013247991 A | 12/2013 |
| WO | WO 99/53988 A1 | 10/1999 |

OTHER PUBLICATIONS

Lavvafi, H., et al. "Flex Bending Fatigue Testing of Wires, Foils, and Ribbons" Materials Science & Engineering A 601 (2014) 123-130.

International Search Report and Written Opinion, PCT Application No. PCT/US2018/028369, dated Jul. 4, 2018, 16 pages.

* cited by examiner

PUSH WIRE FOR ENDOLUMINAL MEDICAL DEVICE

FIELD

This disclosure generally relates to, among other things, endoluminal medical devices and more particularly to push wires for endoluminal medical catheters.

BACKGROUND

A number of medical devices are designed to be navigated through tortuous paths in a human body, such as through a patient's vasculature. The medical devices need to be sufficiently flexible to move through turns in the vasculature yet need to be sufficiently stiff to be pushed through the vasculature. These contrasting properties can present challenges in designing such medical devices.

Endoluminal medical devices are often made from a flexible polymeric catheter containing a lumen into which a push wire is inserted or incorporated to impart stiffness and pushability to the catheter so that the catheter can be pushed through a tortuous path of long distances.

Push wires should be stiff enough to be able to give appropriate levels of push to a device while being flexible enough to track through tortuous anatomy. These often conflicting properties may result in push wires that either kink too easily or are too stiff to easily track through the body.

SUMMARY

This disclosure describes, among other things, push wires for endoluminal medical devices having an improved ability to be navigated through a tortuous path of a long distance, such as through the vasculature of a subject. The push wires have a flexible core surrounded by a stiff sheath.

In some embodiments described herein, a push wire includes an elongate body extending from a proximal end to a distal end. The body includes a core comprising an amorphous metal alloy and includes a sheath that comprises a crystalline metallic material. The sheath intimately surrounds and encapsulates the core.

The amorphous metal alloy of the core may provide for improved flexibility, trackability and kink resistance relative to push wires that are formed from solid crystalline metallic material. The crystalline metallic sheath provides sufficient stiffness to push an endoluminal device through a vessel of a patient. The sheath may be relatively thin yet maintain most of its pushability relative to solid crystalline metallic push wires, as most of the strength of a push wire is derived from the periphery. By way of example, some metal structures may maintain 99% or more of their strength despite having 30% of their interior hollowed out. The sheath may also serve to prevent fracturing of the amorphous core, which may be more brittle than the crystalline sheath.

The materials and relative thicknesses of the core and the sheath may be varied to provide the push wires with appropriate levels of flexibility, kink resistance, and pushability.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

This disclosure generally relates to, inter alia, push wires for endoluminal medical devices having an improved ability to be navigated through a tortuous path of a long distance, such as through the vasculature of a subject. The push wires have a flexible core surrounded by a stiff sheath. The core comprises an amorphous metallic alloy, and the sheath comprises a crystalline metallic material.

The core may be formed from any suitable amorphous metallic alloy. Preferably, the amorphous metallic alloy is biocompatible. However, because the core is surrounded by a sheath, the core may comprise material that is not considered biocompatible. Because amorphous metal alloys or glassy metals are an area of intense development, new amorphous metal alloys are continually being developed. A core of a push wire may comprise any suitable known or future developed amorphous metal alloy. Some examples of suitable amorphous metal alloys include alloys containing one or more of titanium (Ti), zirconium (Zr), copper (Cu), cobalt (Co), barium (Be), nickel (Ni), and aluminum (Al). For example, Ti/Zr alloys, Cu/Zr alloys, Ti/Zr/Cu/Co/Be alloys, Zr/Cu/Ni/Ti/Al alloys, and the like, may be suitable for use as a core of the push wire. U.S. Published Patent Application No. 2002/0162605A1 describes an amorphous metal alloy comprising Zr-17.9%/Cu-14.6%/Ni-5%/Ti-10%/Al, which may be suitable for use in a core of a push wire described herein.

The sheath may be formed from any suitable crystalline metallic material. Preferably, the sheath is formed from biocompatible material. However, because the push wire may be incorporated or inserted in a polymeric catheter in some embodiments, the sheath so enveloped may comprise material that is not biocompatible in such embodiments. Some crystalline metallic materials that may be used for the sheath or a portion thereof include metals (e.g., elemental metals or alloys) that include one or more of palladium (Pd), platinum (Pt), gold (Au), silver (Ag), iridium (Ir), nickel (Ni), titanium (Ti), copper (Cu), tantalum (Ta), iron (Fe), molybdenum (Mo), chromium (CR), zinc (Zn), and the like. In some embodiments, the sheath comprises stainless steel or a titanium alloy comprising one or more of molybdenum, niobium, tantalum, zirconium, chromium, iron and tin. Examples of suitable titanium alloys include Ti—Mo and Ti—Ni alloys. In some embodiments, the sheath comprises a multiphase NiCoCrMo alloy sold under the registered trademark MP35N. Examples of suitable stainless steel alloys include austenitic stainless steels and chromium-nickel steels. Examples of specific stainless steel alloys that may be used include 314 SS (UNS S31400), which has between 23-26% (by weight) Cr, 19-22% Ni, 2% Mn, 1.5-3% Si, 0.25% C, 0.03% S, 0.045% P, with the balance being Fe, and 304V SS (UNS S30400).

Figure 1:
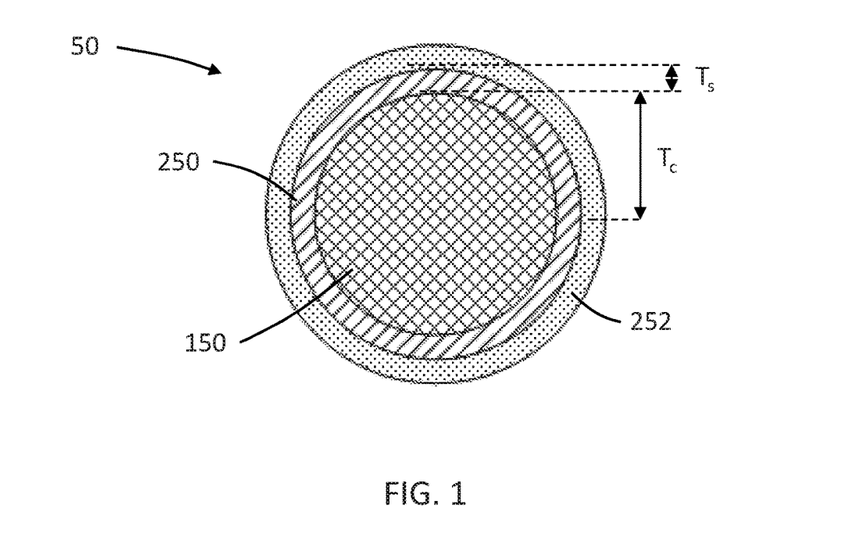
FIG. 1 is a transverse cross-sectional view of an embodiment of a push wire.

The ratio of the radial thicknesses of the core to the sheath, as well as the material of which the core and sheath are formed, may be varied to impart desired properties to the push wires. Referring now to FIG. 1, a transverse cross section of an embodiment of a push wire 50 is shown. The push wire 50 includes a core 150 comprising an amorphous metal alloy and includes a sheath 250 surrounding the core 150. The sheath 250 comprises a crystalline metallic material and may have any suitable radial thickness, $T_s$. The sheath 250 imparts stiffness and pushability to push wire 50. The generally cylindrical core 150 may have any suitable radius or radial thickness, $T_c$. The core 150 imparts kink resistance and flexibility to the push wire 50. By varying the thickness, $T_c$, of the core 150 and the thickness, $T_s$, of the sheath 250, as well as the materials from which the sheath 250 and core 150 are formed, the properties of the push wire 50 may be readily tailored.

The sheath may have any suitable thickness. The thickness of the sheath may vary along the length of the sheath. To maintain pushability, it may be desirable for the thickness of the sheath to remain substantially the same along its length. In some embodiments, the sheath has a thickness of from about 0.2 mm to about 1 mm.

Also depicted in FIG. 1 is an optional slippery or lubricous coating 252 disposed on the sheath 250. Any suitable lubricous coating 252 may be deposited on the sheath 250. Examples of suitable lubricous coatings include hydrogels, diamond-like carbon, or the like. In some embodiments, diamond-like carbon is deposited on a surface of the sheath 250 to form the lubricous coating 252. The lubricous coating 252 may facilitate insertion of the push wire 50 into a lumen of an endoluminal medical device, such as an endoluminal catheter.

The push wires may be made in any suitable manner. In some embodiments, amorphous metal alloys for use in a core of the push wire may be formed by rapid cooling to avoid crystallization of the alloy. The cooling rate to achieve an amorphous metal alloy rather than a crystalline metal alloy depends on a number of factors including the elements included in the alloy and can vary from, for example, 1° K per second to 500° K per second. If the cooling rates are sufficiently low, amorphous alloys may be formed by simple casting, provided that the cast push wire core is sufficiently thin to cool quickly enough to avoid crystal formation.

Amorphous alloy cores for push wires may be injection molded by employing a processes described in, for example, Johnson, et al., "Beating Crystallization in Glass-Forming Metals by Millisecond Heating and Processing," *Science*, vol. 332, pp. 828-822 (13 May 2011).

A sheath may be disposed on the core in any suitable manner. In some embodiments, a crystalline metallic material is disposed on the core by cathode magenetron sputtering as described in, for example, U.S. Pat. No. 4,939,041. Any other suitable coating method, such as atomic layer deposition, physical vapor deposition or the like, may be used to coat a sheath comprising a crystalline metallic material on the core.

In some embodiments, a push wire having an amorphous alloy core and a crystalline metallic sheath may be formed by co-extrusion. For example, processes described in Gravier et al., "New Metallic Glass/Alloy (MeGA) Rods Produced by Co-extrusion," *Advanced Engineering Materials* 8(10):948-953 (24 Oct. 2006) may be employed. As stated by Gravier et al., co-extrusion is a process which has been developed quite extensively to manufacture bimetallic rods and tubes. Gravier et al. further state that the flow characteristics of the two metals depend on many factors related to the geometry of the process and to the flow behavior of the individual metals; and that the extrusion ratio, the die angle, the friction coefficient between the billet and the container, the ratio of the core and sleeve flow stress and the initial bond strength between the two metals are factors controlling the process. Thus, the materials and the thicknesses for the sheath and the core may be readily varied by employing such co-extrusion processes.

In some embodiments, processes employed to produce co-extruded metal-sheathed high-temperature superconductors, which produce a composite rod by simultaneous cladding and consolidation of the core, may be employed to produce a push wire having an amorphous alloy core cladded by a crystalline metallic material.

In some embodiments, an amorphous metal alloy core is formed and the exterior surface is heated and cooled to allow formation of a crystalline metallic sheath. This may be accomplished in any suitable manner. For example, the outer surface of the amorphous core may be laser treated to impart local heating to the surface, allowing the surface to crystallize while the core remains amorphous. Any suitable laser may be employed. For example, a femto laser may be employed to sufficiently heat the surface of the amorphous core to allow subsequent crystallization of the surface.

In some embodiments, the push wire may be formed using drawn filled tube processes. For example, a tube of metallic material may be drawn over a rod of an amorphous alloy to form the push wire. The drawn wire may be heated and annealed. Preferably, the core is not heated to a degree that causes crystallization upon cooling.

An amorphous metal alloy core may be shaped in any suitable manner. For example, electromagnetic pulses may be used to shape the core as described in, for example, Kaltenboeck, et al., "Shaping metallic glasses by electromagnetic pulsing," *Nat. Commun.* 7:10576 (Published online 8 Feb. 2016).

The push wires may have any suitable dimensions. The dimensions of the push wires may be dependent on the dimensions of the endoluminal medical device with which the push wires are employed. In some embodiments, the push wires have a length from about 20 cm to about 200 cm, such as from about 50 cm to about 150 cm. By way of example, a push wire may have a length of about 121 cm when used with an endoluminal catheter of about 150 cm long. A distal portion of the push wire may be tapered to a reduced diameter distal end. The tapered distal portion may have any suitable length. For example, the tapered portion may have a length of about 5 cm to about 25 cm, such as about 10 cm. The proximal portion may have any suitable diameter. For example, the proximal portion of the push wire may have a diameter in a range from about 0.005 inches to about 0.08 inches, such as from about 0.010 inches to about 0.07 inches. The distal portion may be tapered down to any suitable diameter. For example, the distal portion may be tapered down to a range from about 0.001 inches to about 0.070 inches, such as from about 0.002 to about 0.06 inches.

Figure 2:
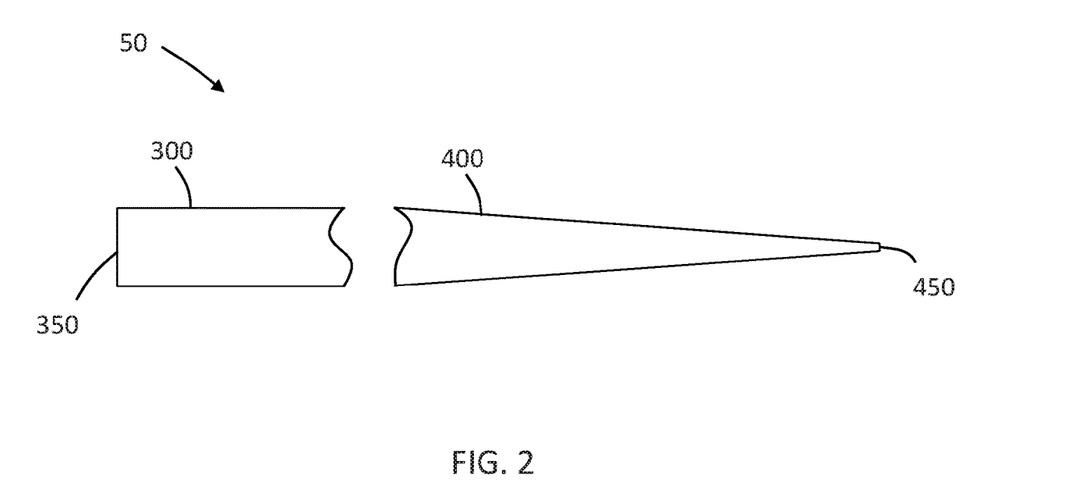
FIG. 2 is schematic plan view of an embodiment of a push wire.

Referring to FIG. 2 a schematic plan view of an embodiment of push wire 50 is shown. The push wire 50 has an elongate body extending from a proximal end 350 to a distal end 450. The body of the depicted push wire 50 has a proximal portion 300 that has a substantially uniform outer diameter and a distal portion 400 that tapers from the outer diameter of the proximal portion 300 to a reduced diameter at the distal end 450.

Push wires having tapered distal end portions may be formed in any suitable manner. In some embodiments, the core and sheath may be co-extruded through dies having controllably variable orifices. The distal portion may be tapered by reducing the orifices of the dies as the distal portion is being extruded. Alternatively, an amorphous core material of a substantially constant diameter may be extruded and the distal end portion of the core may be ground to the desired taper. A material may be deposited on the ground core to form the sheath. Another option is to cast the amorphous core to the desired shape and deposit the sheath on the core.

The push wires may have any suitable properties to allow the push wire to push an endoluminal medical device, such as an endoluminal catheter, or to allow the endoluminal medical device containing the push wire to be pushed, through a lumen of a subject, such as the vasculature of the subject.

In some embodiments, the push wire may have a pushability of 50 gf (gram-force) or greater, such as 100 gf or greater or 200 gf or greater. In many embodiments, the push wire may have a pushability in a range from about 50 gf to about 450 gf. Pushability of a push wire may be tested in any suitable manner. For example, pushability may be tested by using a distal load cell to measure the amount of force applied to the distal tip when the proximal end is advanced forward at a constant velocity (1 mm/s) until the wire kinks. The values provided above are values that may be obtained when applying an increasing load to the proximal end of the push wire until the kinking occurs.

Pushability may be a function of cross sectional area of a push wire. A push wire as described herein may have any suitable pushability per cross sectional area, such as from about 38,750 gf/cm$^2$ to about 232,500 gf/cm$^2$. In some embodiments, a push wire as described herein has pushability per cross sectional area of greater than about 116,250 gf/cm$^2$, or in a range from about 116,250 gf/cm$^2$ to about 232,500 gf/cm$^2$.

In some embodiments, the push wire may have improved flexibility or kink resistance relative to currently available push wires when the push wire is wrapped around increasingly smaller diameter mandrels until the push wire kinks. Such flexibility or kink resistance may be determined as described in the U.S. Food and Drug Administration document "Guidance for Industry and FDA Staff—Non-Clinical Engineering Tests and Recommended Labeling for Intravascular Stents and Associated Delivery Systems" (issued on Apr. 18, 2010; see Section C-9 re: reduced radius mandrel test).

Push wires having such improved flexibility and pushability may be superior, in various aspects, to currently available push wires, which often do not have less desirable properties in one or two of these areas. For example, currently available push wires that are highly pushable, tend to suffer from poor flexibility and kink resistance.

Push wires described herein may be used to push any suitable medical device through a subject or may be incorporated into any medical device to increase pushability of the device through a lumen of a subject. In many embodiments, a push wire is incorporated or inserted in an endoluminal medical catheter. In such embodiments, the push wire may be considered a push wire or a core wire. The push wires may be incorporated in a balloon dilation catheter, coronary stent delivery catheter, or the like.

For purposes of example, embodiments of a push wire according to the present disclosure are described below with regard to FIGS. 3-12 in the context of a dilation catheter, such as a dilation catheter described in U.S. Pat. No. 5,823,995. It will be understood that the push wires described herein may be used with any other suitable endoluminal device.

Figure 3:
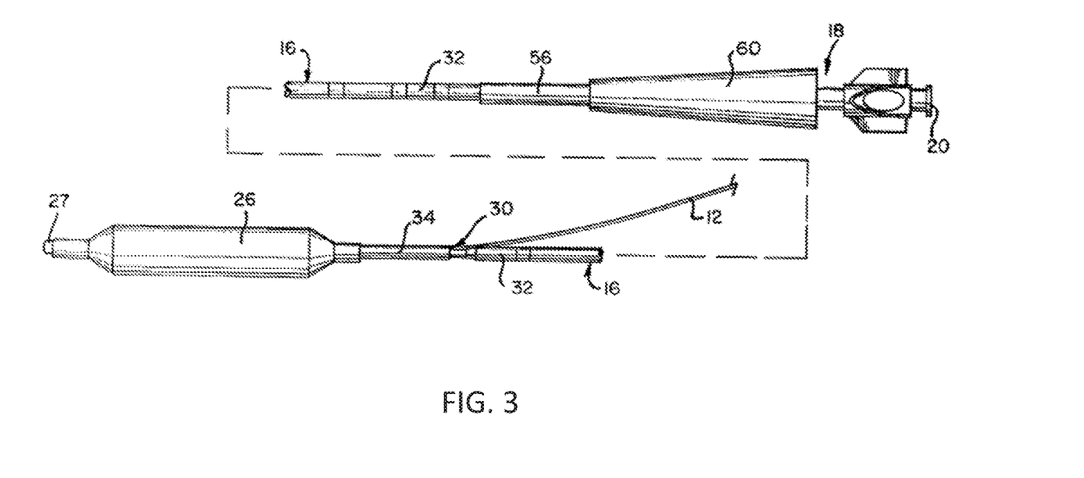
FIG. 3 is a schematic plan view of an embodiment of a dilation catheter that may employ a push wire as described herein.
Figure 4:
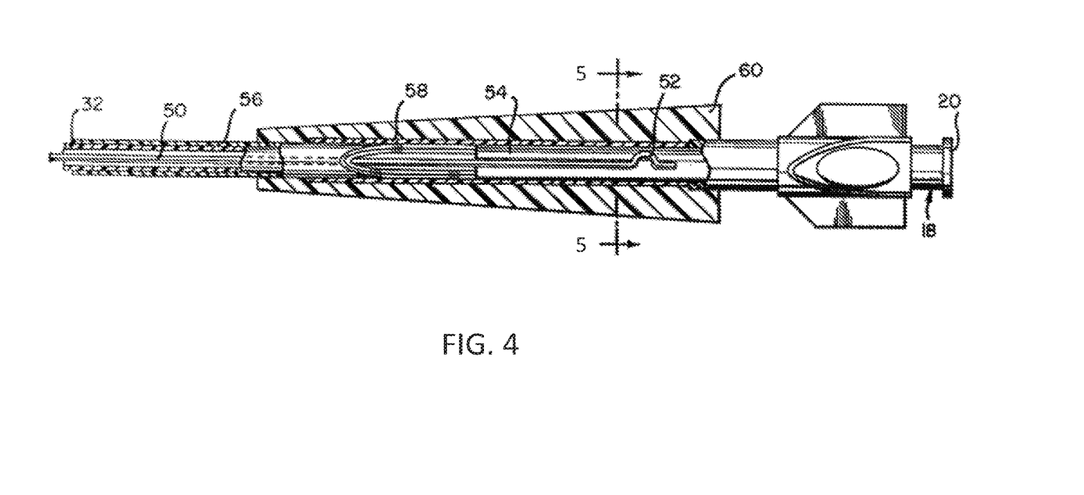
FIG. 4 is a schematic plan view partially in longitudinal section showing one way in which a push wire may be anchored in a luer fitting.
Figure 5:
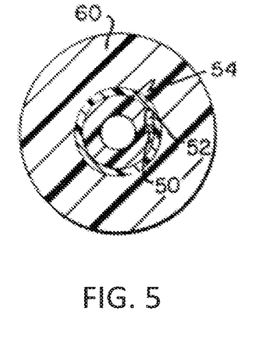
FIG. 5 is a transverse sectional view along the line 5-5 of FIG. 4.

Referring now to FIGS. 3-5, a dilation catheter comprises an elongated tubular shaft 16 having a proximal shaft 32 and a distal shaft 34. The distal shaft overlaps the proximal shaft in such a way as to form a guide wire port 30 through which a guide wire 12 can be introduced in conventional fashion. The lumen for the guide wire 12 is formed by an inner tube 14 which may be made of the same material as distal shaft 34, e.g., a flexible heat shrinkable material such as high density polyethylene. Inner tube 14 extends from a point just proximal of the guide wire port 30 to the distal end of the balloon 26. The proximal end of shaft 32 is connected to a luer fitting 18. A dilatation balloon 26, which may be of convention design, is secured at the distal end of the shaft 34. Fluid introduced through a connector 20 of luer 18 causes balloon 26 to expand in conventional fashion.

Figure 6:
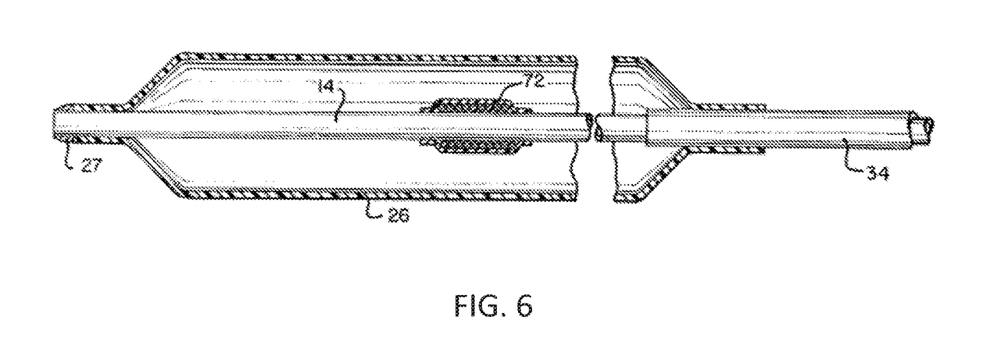
FIG. 6 is a plan view partially in section showing how the dilatation balloon is secured to the distal end of the catheter of FIG. 3.

In some embodiments, the annular space 24 between the distal shaft 34 and inner tube 14 forms an inflation lumen. The shaft 34 terminates proximal to the distal end of the inner tube 14 (FIG. 6). As shown in FIG. 6, the proximal end of balloon 26 is connected and sealed to the distal end of the distal shaft 34. The inner tube 14 extends through the balloon 26 and is sealed at its distal end to the distal end of the balloon. Adhesive 29 provides a rounded end at the distal end of the balloon 26.

A radiopaque coil spring 72 is positioned within the balloon 26 around the inner tube 14 (FIG. 6). The coil spring 72 ensures flexibility of the balloon, the distal portion of the catheter, and the tip. The radiopaque coil spring enables the balloon 26 to be identified under X-ray.

A push wire 50, tapered at its distal end, extends from the luer 18 axially through proximal shaft 32 to the vicinity of the guide wire port 30 where it is positioned within the inner tube 14. The tapered end of the push wire 50 is anchored within the proximal end of inner tube 14. In the depicted embodiment, the tapered end of the push wire 50 includes five adhesive beads 27 and is anchored within the proximal end of inner tube 14 by heat shrinking the inner tube.

However, the tapered end of the push wire 50 may be anchored within the proximal end of inner tube 14 in any other suitable manner.

Figure 7:
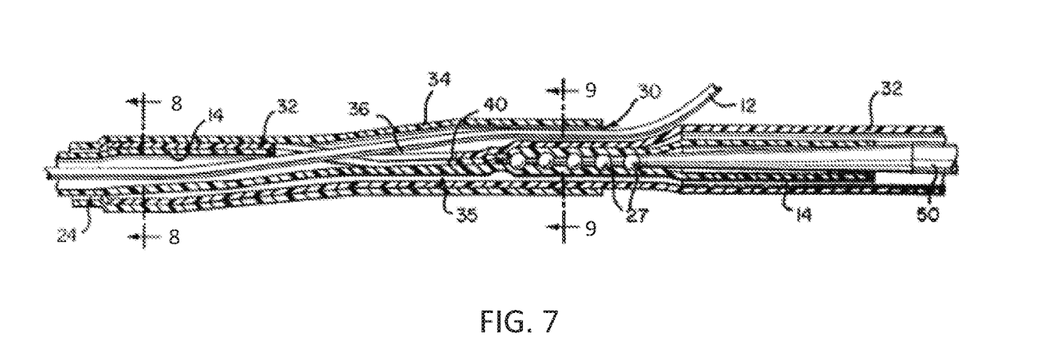
FIG. 7 is a schematic cross-sectional view of a catheter showing a fused laminate in the region of the guide wire port.
Figure 8:
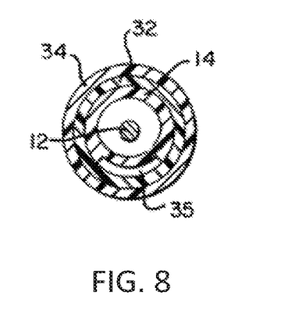
FIG. 8 is a transverse sectional view along the line 8-8 of FIG. 7.
Figure 9:
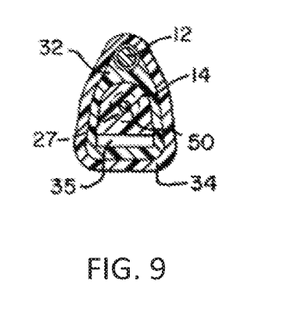
FIG. 9 is a transverse sectional view along the line 9-9 of FIG. 7.

In the depicted embodiment, slots 40 and 36 are cut in inner tube 14 and proximal shaft 32, respectively, so that the guide wire 12 can be inserted through the port 30 and into the lumen within inner tube 14 distal of port 30. As shown in FIGS. 7-9, the inner tube 14 may be bonded to a distal portion of the proximal shaft 32 and the distal shaft 34 to form a tubular laminate. Since fluid is introduced into the balloon in the passageway 24 between the inner tube 14 and the distal shaft 34, a fluid passageway 35 is provided from the proximal shaft 32 through the thermally bonded section of the catheter into the region where the distal shaft 34 and inner tube 14 are coaxial. This region starts at the left-hand side of FIG. 5 and extends into the balloon where the distal shaft 34 terminates.

FIG. 4 shows one way in which the proximal end of the push wire 50 may be anchored within the luer fitting 18. The luer fitting 18 includes a cylindrical balloon leg 54, its distal end abutting against the proximal end of the proximal shaft 32. The push wire 50 includes a crimp 52 at its proximal end which passes through the wall of balloon leg 54 so that the crimped portion lies against the exterior surface of the balloon leg 54. Wire 50 is positioned within the balloon leg 54 during the molding process. A strain relief tube 56 envelops the proximal shaft 32 distal of its junction with the balloon leg 54. A shrink tube 58 is placed over the crimped portion of wire 50 and a proximal section of strain relief tube 56 and serves to secure the assembly when heat is applied. The luer may also include a conically shaped cover 60 which is secured to the luer by conventional adhesives and serves partly as a strain relief member.

The precise point at which the push wire 50 terminates is not critical but it is preferred that the push wire terminate in the vicinity of the guide wire port 30.

An embodiment for assembling a catheter including a push wire as described herein is as follows. First, the adhesive beads 27 are applied to the distal end of the push wire 50 and cured. Push wire 50 is then inserted into the inner tube 14 with a patency mandrel between the wire and tube in the area where the tube and wire are not to be bonded together. A shrink tube is then placed over the assembly and the inner tube 14 heat welded to the push wire 50. The shrink tube and patency mandrel are removed.

Figure 10:
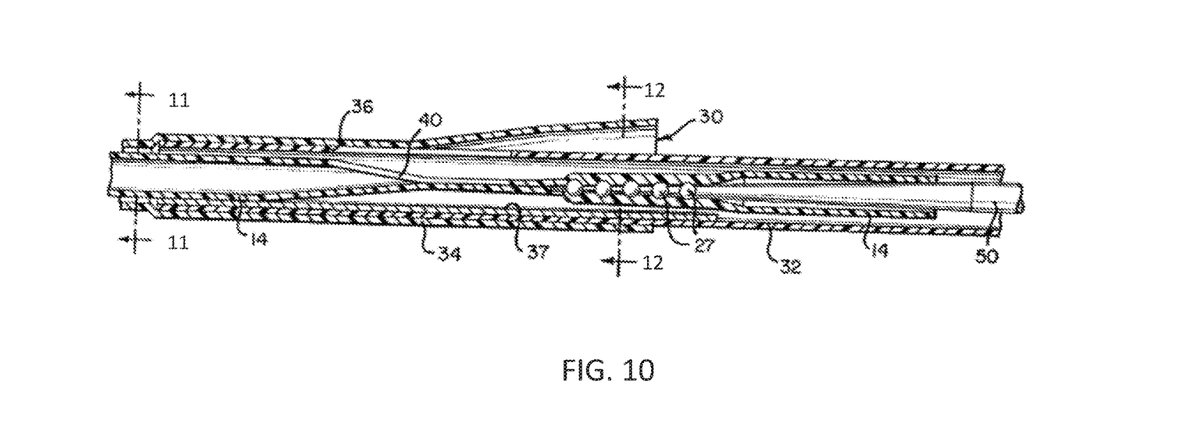
FIG. 10 is a schematic sectional view showing an embodiment of an inner tube with a retained push wire inserted into a catheter shaft prior to a final assembly step in which a fused laminate is formed.
Figure 11:
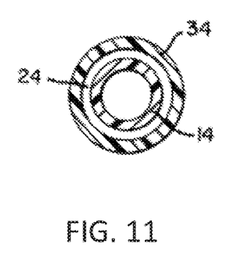
FIG. 11 is a transverse sectional view along the line 11-11 of FIG. 10.
Figure 12:
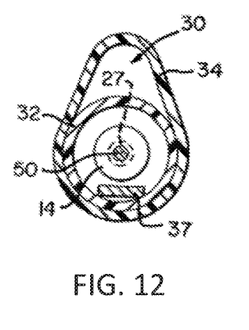
FIG. 12 is a transverse sectional view along the line 12-12 of FIG. 10.

As shown in FIGS. 10-12, the push wire assembly thus formed is then placed in the proximal shaft 32. The proximal end of wire 50 is attached to luer 18 as described above and heat welded into position.

Next, a flat mandrel 37 is positioned between inner tube 14 and proximal shaft 32 to provide for the fluid passageway 35 through the fused laminate after heat welding. Similarly, a patency mandrel (not shown) is positioned in the inner tube 14 to maintain an opening for the guide wire 12. A shrink tube is positioned over this assembly and heat applied to weld the inner tube 14 to proximal shaft 32. The shrink tube and patency mandrel are then removed.

Slots 36 and 40 are then cut through the proximal shaft 32 and inner tube 14 to provide an opening for the guide wire into the lumen within the inner tube 14. A patency mandrel is then placed within the inner tube extending through the slots. The flared distal shaft 34 is inserted over the distal end of the proximal shaft 32 and up over the slots and patency mandrel with the proximal end of the distal shaft 32 overlapping the push wire 50. The shrink tube is applied over the joint area and heat applied to weld the entire assembly to form the fused laminate. The shrink tube is removed and then the patency mandrel and flat mandrel 37 are removed leaving the fused laminate with a guide wire port into the inner tube 14 and the fluid passageway 35 through the fused laminate.

During the welding process, the portion of proximal shaft 32 just proximal of slot 36 is "folded down" into contact with the wire retention section of inner tube 14 to form a sloped wall (FIG. 7). The close positional relation among the guide wire opening 40 of the inner tube 14, the guide wire entrance port 30, and the sloped wall of the proximal shaft 32 forms a smooth transition and passageway for the guide wire into the inner tube 14. The smooth transition and passageway not only aids in initial guide wire placement into the catheter, but also facilitates catheter exchange.

The dilatation catheter described above regarding FIGS. 3-12 is presented merely for purposes of illustration and not limitation. It will be understood that the push wires described herein may be used in connection with, or be a part of, any suitable endoluminal medical device.

Thus, embodiments of PUSH WIRE FOR ENDOLUMINAL MEDICAL DEVICE are disclosed. One skilled in the art will appreciate that the apparatuses, systems and methods described herein can be practiced with embodiments other than those disclosed. The disclosed embodiments are presented for purposes of illustration and not limitation. One will also understand that components of the associated devices and systems depicted and described with regard the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

We claim:

1. A push wire for an endoluminal medical device, comprising:
   an elongate body extending from a proximal end to a distal end,
   wherein the body includes (i) a cylindrical core comprising an amorphous metal alloy, and (ii) a sheath comprising a crystalline metallic material, wherein the sheath surrounds the core,
   wherein the sheath provides sufficient stiffness to push the endoluminal device through a vessel of a patient, and
   wherein the core imparts kink resistance and flexibility.

2. The push wire of claim 1, wherein the body has a pushability of 50 gf or greater.

3. The push wire of claim 2, wherein the body has a pushability of 100 gf or greater.

4. The push wire of claim 3, wherein the body has a pushability of 200 gf or greater.

5. The push wire of claim 1, wherein the body has a pushability per cross sectional area of 250,000 gf/in$^2$ or greater.

6. The push wire of claim 1, wherein the body has a pushability per cross sectional area of 750,000 gf/in$^2$ or greater.

7. The device of claim 1, wherein the core consists essentially of the amorphous metal alloy.

8. The device of claim 1, wherein the amorphous metal alloy comprises an alloy comprising zirconium.

9. The device of claim 1, wherein the crystalline metallic material comprises a crystalline metal alloy.

10. The device of claim 9, wherein the crystalline metal alloy comprises stainless steel.

11. The device of claim 9, wherein the crystalline metal alloy comprises titanium.

12. The device of claim 6, further comprising a lubricous coating disposed on the sheath.

13. The device of claim 6, wherein the coating comprises diamond-like carbon.

14. The device of claim 1, wherein the sheath has a thickness of from about 0.2 mm to about 1 mm.

15. The device of claim 1, wherein the body includes a distal portion, wherein the distal portion is tapered in proximity to the distal end.

16. The device of claim 15, wherein the tapered portion of the distal portion has a length in a range of from 5 cm to 25 cm.

17. The device of claim 1, wherein the body has a length of in a range from 50 cm to 200 cm.

18. An endoluminal delivery assembly comprising:
   a push wire according to claim 1; and
   a catheter comprising a first lumen configured to receive at least the distal portion of the body of the device according to claim 1.

19. An endoluminal delivery assembly comprising:
   a push wire according to claim 1; and
   a catheter comprising a polymeric material to which at least a distal portion of the push wire is anchored.

20. The assembly of claim 19, wherein the assembly is a percutaneous coronary intervention assembly.

21. The endoluminal delivery assembly of claim 18, wherein the catheter further comprises a second lumen configured to receive a guidewire.

* * * * *